United States Patent [19]

Ainsworth et al.

[11] Patent Number: 5,494,154
[45] Date of Patent: Feb. 27, 1996

[54] SURGICAL SUTURE PACKAGE

[75] Inventors: Gary Ainsworth; Brian K. Gourley, both of Ada, Okla.

[73] Assignee: Look Incorporated, Norwell, Mass.

[21] Appl. No.: 273,946

[22] Filed: Jul. 12, 1994

[51] Int. Cl.[6] ................................................. A61B 17/06
[52] U.S. Cl. ........................ 206/63.3; 206/382; 206/227
[58] Field of Search ................................ 206/63.3, 380, 206/382, 495, 227

[56] References Cited

U.S. PATENT DOCUMENTS

| | | |
|---|---|---|
| 268,811 | 5/1883 | Black . |
| 3,444,994 | 5/1969 | Kaepernik et al. . |
| 4,034,850 | 7/1977 | Mandel et al. . |
| 4,089,409 | 5/1978 | Cerwin . |
| 4,135,623 | 1/1979 | Thyen . |
| 4,142,628 | 3/1979 | Marocco et al. ........................ 206/63.3 |
| 4,249,656 | 2/1981 | Cerwin et al. ........................ 206/63.3 |
| 4,253,563 | 3/1981 | Komarnycky ........................ 206/63.3 |
| 4,391,365 | 7/1983 | Batchelor . |
| 4,412,613 | 11/1983 | Kubas ................................... 206/63.3 |
| 4,412,614 | 11/1983 | Ivanov et al. ........................ 206/63.3 |
| 4,483,437 | 11/1984 | Cerwin et al. ........................ 206/63.3 |
| 4,491,218 | 1/1985 | Aday . |
| 4,533,041 | 8/1985 | Aday et al. . |
| 4,555,016 | 11/1985 | Aday et al. ........................... 206/63.3 |
| 4,700,833 | 10/1987 | Smith ..................................... 206/380 |
| 4,896,767 | 1/1990 | Pinheiro . |
| 4,946,043 | 8/1990 | Roshdy et al. ........................ 206/63.3 |
| 5,024,322 | 6/1991 | Holzwarth . |
| 5,048,678 | 9/1991 | Chambers . |
| 5,121,836 | 6/1992 | Brown et al. ........................ 206/63.3 |
| 5,127,518 | 7/1992 | Holzwarth et al. . |
| 5,199,561 | 4/1993 | Roshdy et al. ........................ 206/63.3 |
| 5,249,673 | 10/1993 | Sinn . |

*Primary Examiner*—Paul T. Sewell
*Assistant Examiner*—Marie Denise Patterson
*Attorney, Agent, or Firm*—Fish & Richardson

[57] ABSTRACT

An elongated, folded paper package for containing surgical suture material and needles. The package includes folding panels which cover and protect the suture material, winding pin holes to assist in winding suture material, a foam block to hold the needles securely, one slit to hold the package closed and additional slits for ease of opening the package to expose the needles.

13 Claims, 3 Drawing Sheets

SURGICAL SUTURE PACKAGE

BACKGROUND OF THE INVENTION

The present invention relates to the field of packaging sutures for surgical use.

A variety of packaging methods for suture materials have been devised to address such problems as tangling of threads, elimination of dust and particulates, accessibility of needles, and ease of use. Most packaging materials are made out of a stiff paperboard which can be cleaned and sterilized, and are folded in various ways to enhance product delivery.

Solutions to tangling problems have included winding the suture in loops or figure eights, interleaving looped suture with cards, and winding the suture tightly around pins that fit through holes in the paperboard during packaging. Needle accessibility is often achieved by placing the needles in a designated portion of the package, sometimes in a foam block, and tearing off that portion to expose the needles.

SUMMARY OF THE INVENTION

In one aspect, the invention features, in general, a package for surgical sutures made of sheet material that has an elongated central panel with two holes for insertion of winding pins during assembly of the product. The first winding pin hole is near one end of the central panel, and the second is closer to the other end. Additionally, there are two or more panels that fold over the central panel: a first panel is connected to the central panel by a fold joint and covers the area between the two holes when folded. A second panel completely covers the winding pin holes when folded. With this construction, the suture is held securely in position during suture winding and panel folding following removal of the winding pins, and does not tangle or unwind during shipping or storage.

In another aspect, the invention features, in general, a package for surgical sutures made of sheet material that has an elongated central panel and two groups of holes for insertion of winding pins during assembly of the product. The first group of winding pin holes is near one end of the central panel, and the second group is closer to the other end. The pins in each group of winding pin holes are substantially spaced from each other (more than one-half the width of the panel), so that the suture material may be wound loosely in wide loops that reduce "memory" of the suture, especially monofilament suture materials. Additionally, there are two or more panels that fold over the central panel.

In preferred embodiments, the packages have an additional flap at the end of the central panel. The package also has a slit on one panel which receives the edge of another panel in order to hold the package closed in the folded configuration. An adhesive-backed label is applied over the panel holding the package closed in order to provide a tamper-evident seal. Additional slits are provided in a panel to allow the package to easily be torn open to expose the needles and/or suture material. A foam block is attached to the central panel near the region of the opening slits in order to hold the needles of the suture material securely. The suture material may be wound in a figure eight configuration around the winding pins in the single or group winding pin hole arrangement. Other advantages of the invention will be apparent from the following description of the preferred embodiment thereof and from the claims.

DESCRIPTION OF THE PREFERRED EMBODIMENTS

The following is a description of one preferred embodiment. This description is not intended to be limiting.

Structure

Figure 1:
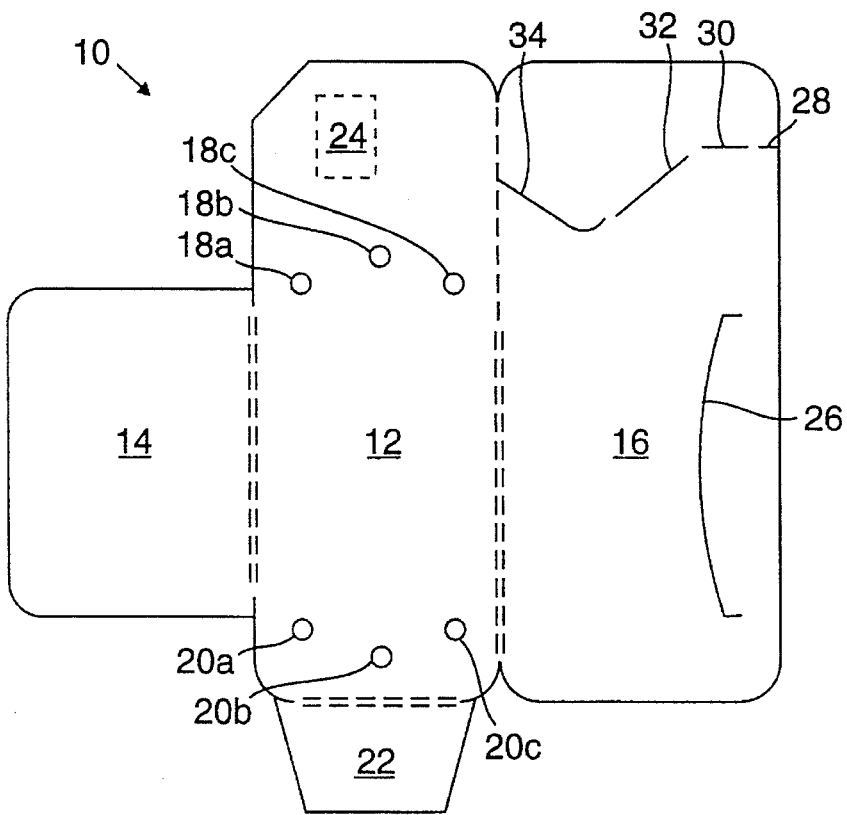
FIG. 1 is a plan view of an unfolded suture package according to the invention.

Referring to FIG. 1, package 10 includes central panel 12, attached to which are side panels 14, 16, and 22 by fold joints. Central panel 12 has winding pin holes 18a–c and 20a–c, and foam square 24 adhesively mounted thereon. Central panel 12 has the dimensions 1.4"×3.6". Side panel 14 has the dimensions 1.4"×1.9". Side panel 16 has a long curved slit 26 (approximately 1.8" in length) and four additional slits 28, 30, 32, and 34 across the top all arranged along a tear line. Side panel 16 has the dimensions 1.6"× 3.6". Bottom panel 22 has downwardly converging outward edges 36. Its dimensions are 0.6"×1.1– 0.8" (attached base to outer edge). The dimensions of central panel might be individually or jointly increased or decreased up to 50%, with corresponding changes to the dimensions of the other panels.

Package 10 is made of stiff paperboard.

Use

Figure 2:
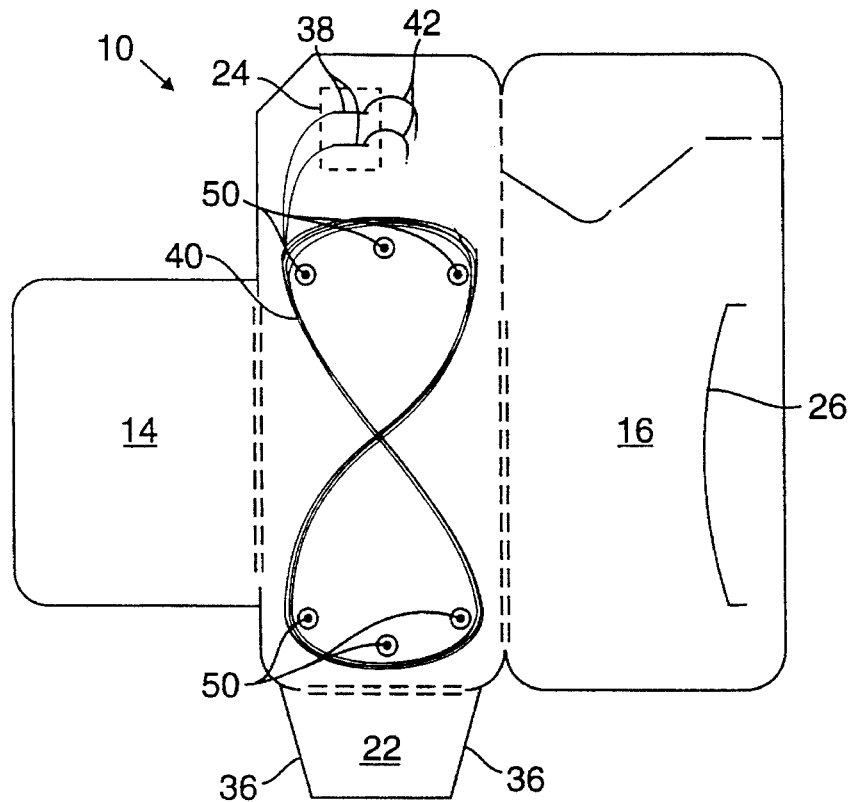
FIG. 2 is a plan view showing needles and suture material arranged in the FIG. 1 package mounted on a fixture with winding pins prior to package folding.

In use, package 10 is mounted on a fixture such that pins 50 pass through winding pin holes 18a–c and 20a–c (FIG. 2). Needles 42 attached to suture material 40 are placed into foam block 24 of package 10 via slits 38 in foam block 24. Suture material 40 is wound around pins 50 in a figure eight configuration.

Holes 18a–c extend across greater than one-half the width of central panel 12 (in fact, the holes are 1.0" apart, about 80% of the width), providing for a large radius of curvature for suture material wound in a figure eight configuration.

Figure 3:
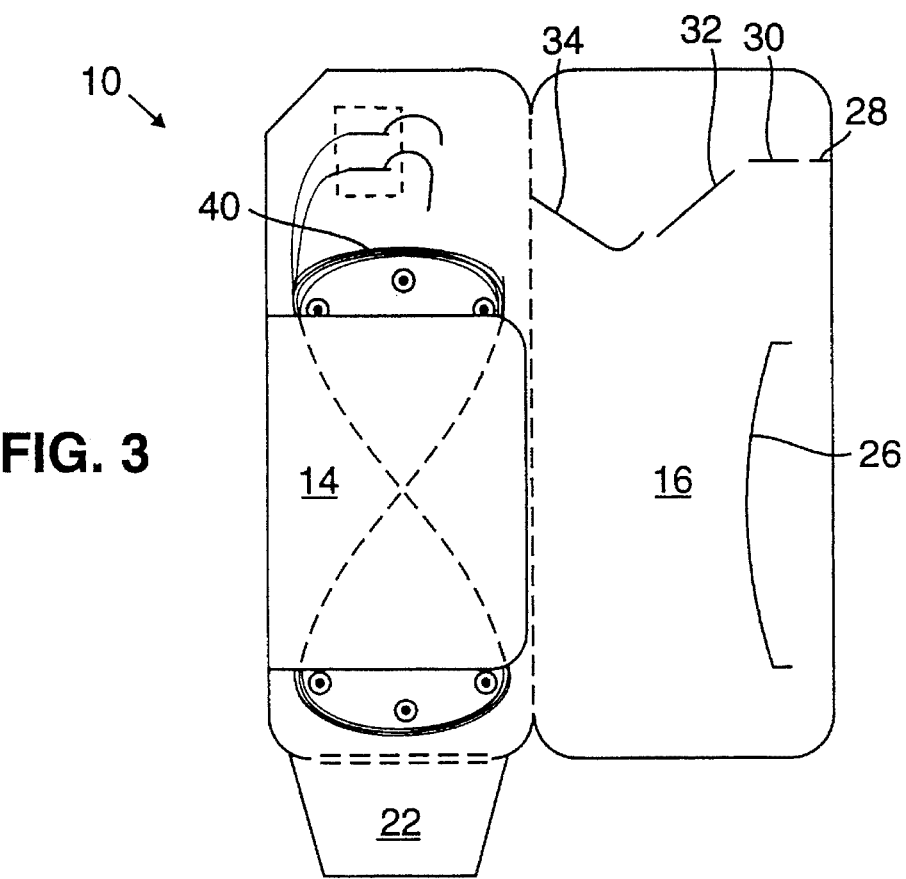
FIG. 3 is a plan view of the FIG. 1 package showing one panel folded over a central panel and suture material between winding pins.
Figure 4:
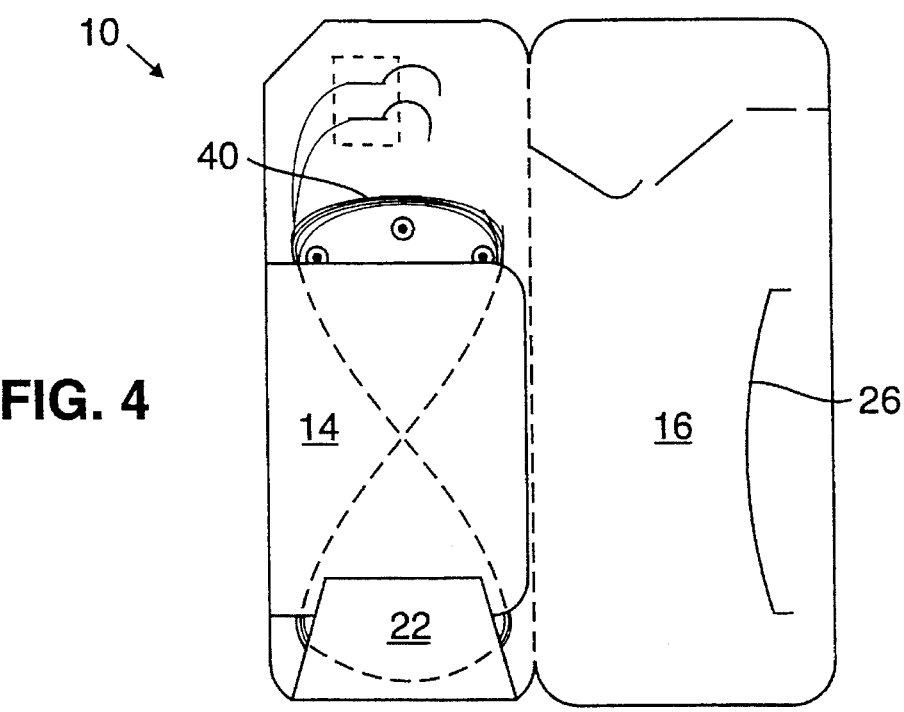
FIG. 4 is a plan view of the FIG. 1 package showing a bottom panel folded over the suture material and overlapping the first folded panel.
Figure 5:
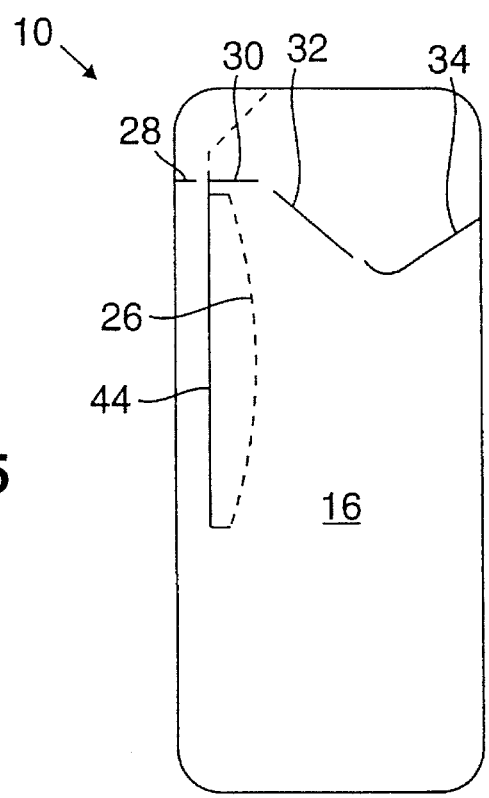
FIG. 5 shows the fully folded surgical suture package according to the invention.

Referring to FIG. 3, panel 14 is folded over central panel 12 and suture material 40, securing the intersecting portions of the suture material thereunder. The package is then removed from the fixture, and side panel 22 is folded over, covering holes 20a–c and securing the end portion of the suture thereunder (FIG. 4). FIG. 5 shows panel 16 folded over panels 12, 14, and 22. Slit 26 engages edge 44 to hold package 10 closed, and is covered with an adhesive backed label (not shown) which provides a tamper proof seal.

Figure 6:
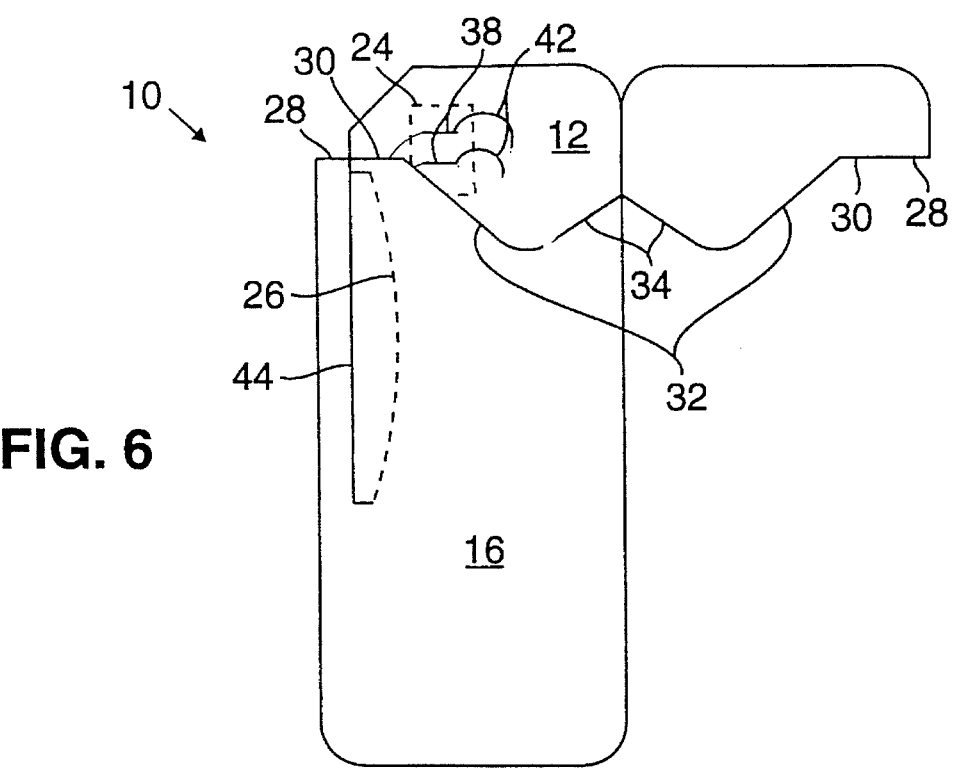
FIG. 6 depicts the FIG. 5 package after opening along tear slits to expose the needles for use.

FIG. 6 shows the opened package 10. It has been torn open starting at slit 28 and further along slits 30, 32, and 34. In the open configuration, needles 42 are exposed and ready for use.

Package 10 allows ease of opening via slits 28–34, and access to needles 42. The suture material 40 has a figure eight configuration with large curvature having reduced memory and allows removal of suture material 40 through the opening created by slits 28–34 without tangling. Covering panel 16 offers protection for needles 42 and suture material 40.

What is claimed is:

1. A package for surgical sutures comprising a central panel that is elongated along a longitudinal axis and has two parallel sides that are longer than its width, two or more first winding pin holes at one end, and two or more second winding pin holes closer to the other end, said holes at one end being spaced by substantially more than half said width such that a suture wound on pins extending therethrough is near said parallel sides, a unitary first panel connected to said central panel by a fold joint along a said parallel side, said first panel having dimensions along substantially all axes parallel to said longitudinal axis that are less than the distance between said first and second holes along said longitudinal axis such that said first panel substantially covers the region between said first and second holes when folded over said central panel but leaves said holes exposed, and one or more additional panels connected to said central panel by a respective fold joint so as to cover both of said holes when folded over.

2. The package of claim 1 further comprising a further panel that is connected to said central panel by a fold joint and covers one said winding pin hole.

3. The package of claim 1 wherein one of said additional panels has a slit that receives an edge of said central panel to hold said package closed.

4. The package of claim 1 wherein said central panel has a needle supporting area, and one of said additional panels has a series of tear slits across the width of said additional panel so as to expose said needle supporting area.

5. The package of claim 1 wherein said package further comprises an adhesively applied foam block on said central panel for retaining a needle.

6. The package of claim 1 further comprising a surgical suture wound around said winding pin holes in a figure eight configuration.

7. A package for surgical sutures comprising a central panel that is elongated along a first axis and has a first group of winding pin holes at one end and a second group of winding pin holes closer to the other end, the distance between at least two holes in each group along a second axis perpendicular to said first axis being greater than one-half the width of said central panel along said second axis, two of said holes in each said group being spaced along said second axis by about 80% of the width of said central panel, each group including a third hole spaced outward of said two holes along said first axis, and one or more additional panels connected to said central panel by a respective fold joint so as to cover both groups of said holes when folded over.

8. The package of claim 7 further comprising a surgical suture wound around said winding pin holes in a figure eight configuration.

9. The package of claim 7 further comprising a panel connected to said central panel by a fold joint such that said further panel covers the region between said two groups of holes when folded over said central panel but leaves said holes exposed.

10. The package of claim 7 further comprising a further panel that is connected to said central panel by a fold joint and covers one said group of winding pin holes.

11. The package of claim 7 wherein one of said additional panels has a slit that receives an edge of said central panel to hold said package closed.

12. The package of claim 7 wherein said central panel has a needle supporting area, and one of said additional panels has a series of tear slits across width of said additional panel so as to expose said needle supporting area.

13. The package of claim 7 wherein said package further comprises an adhesively applied foam block on said central panel for retaining a needle.

\* \* \* \* \*

UNITED STATES PATENT AND TRADEMARK OFFICE
CERTIFICATE OF CORRECTION

PATENT NO. : 5,494,154

DATED : February 27, 1996

INVENTOR(S) : Gary Ainsworth et al.

It is certified that error appears in the above-identified patent and that said Letters Patent is hereby corrected as shown below:

> Title page:
> Please add the following under References Cited:
>
> --FOREIGN PATENT DOCUMENTS--
>
> --2-217996    8/90    Japan--

Signed and Sealed this

Seventeenth Day of December, 1996

Attest:

BRUCE LEHMAN

*Attesting Officer*        *Commissioner of Patents and Trademarks*